(12) United States Patent
Chakravarthy et al.

(10) Patent No.: US 11,291,746 B2
(45) Date of Patent: *Apr. 5, 2022

(54) WOUND DRESSING CONTAINING HONEY AND COLLAGEN

(71) Applicant: Medline Industries, LP, Northfield, IL (US)

(72) Inventors: Debashish Chakravarthy, Vernon Hills, IL (US); Andrew J. Ford, Libertyville, IL (US)

(73) Assignee: Medline Industries, LP, Northfield, IL (US)

(*) Notice: Subject to any disclaimer, the term of this patent is extended or adjusted under 35 U.S.C. 154(b) by 328 days.

This patent is subject to a terminal disclaimer.

(21) Appl. No.: 16/460,911

(22) Filed: Jul. 2, 2019

(65) Prior Publication Data

US 2019/0321509 A1    Oct. 24, 2019

Related U.S. Application Data

(63) Continuation of application No. 14/031,716, filed on Sep. 19, 2013, now Pat. No. 10,342,891.

(51) Int. Cl.
| | | |
|---|---|---|
| *A61L 15/44* | (2006.01) | |
| *A61L 15/32* | (2006.01) | |
| *A61L 15/40* | (2006.01) | |
| *A61L 15/18* | (2006.01) | |

(52) U.S. Cl.
CPC ............ *A61L 15/44* (2013.01); *A61L 15/18* (2013.01); *A61L 15/325* (2013.01); *A61L 15/40* (2013.01); *A61L 2300/404* (2013.01); *A61L 2300/41* (2013.01); *A61L 2300/412* (2013.01); *A61L 2300/434* (2013.01)

(58) Field of Classification Search
CPC .............. A61F 13/00063; A61F 13/069; A61F 2013/00157; A61F 2013/00161; A61F 2013/00519; A61F 2013/00523; A61F 2013/00927; A61F 2013/00936
See application file for complete search history.

(56) References Cited

U.S. PATENT DOCUMENTS

| | | | |
|---|---|---|---|
| 10,342,891 B2 * | 7/2019 | Chakravarthy | A61L 15/325 |
| 2004/0127826 A1 * | 7/2004 | Caskey | A61P 17/02 |
| | | | 602/41 |
| 2005/0013987 A1 * | 1/2005 | Carr | A61F 13/00991 |
| | | | 428/304.4 |
| 2005/0256437 A1 * | 11/2005 | Silcock | A61F 13/0203 |
| | | | 602/48 |
| 2006/0159732 A1 * | 7/2006 | Cullen | A61L 15/46 |
| | | | 424/445 |

(Continued)

FOREIGN PATENT DOCUMENTS

GB    2497121 A  *  6/2013  ....... A61F 13/00991

*Primary Examiner* — Adam Marcetich
(74) *Attorney, Agent, or Firm* — Gurr Brande & Spendlove, PLLC; Robert Dan Spendlove

(57) ABSTRACT

A wound dressing makes use of a saccharide, such as Manuka honey, in combination with collagen in order to suppress the efficacy of matrix metalloproteinases enzymes ("MMPs") present in chronic wounds. The mixture is applied to an absorbent surface that is designed to absorb the mixed saccharide only partially.

17 Claims, 1 Drawing Sheet

(56) References Cited

U.S. PATENT DOCUMENTS

| | | | |
|---|---|---|---|
| 2007/0140984 A1* | 6/2007 | Kusano | A61K 31/7016 424/70.13 |
| 2010/0262090 A1* | 10/2010 | Riesinger | A61F 13/00046 604/304 |
| 2011/0052665 A1* | 3/2011 | Hardy | A61P 7/04 424/445 |
| 2012/0061267 A1* | 3/2012 | Villalobos | A61F 13/15203 206/223 |
| 2012/0116279 A1* | 5/2012 | Munro | A61L 15/60 602/43 |
| 2012/0225105 A1* | 9/2012 | Swanzy | A61Q 19/00 514/23 |
| 2013/0131701 A1* | 5/2013 | Komlos | A61L 31/047 606/151 |
| 2013/0310781 A1* | 11/2013 | Phillips | C08L 83/04 604/319 |
| 2014/0163447 A1* | 6/2014 | Wieland | A61L 15/325 602/47 |
| 2015/0018791 A1* | 1/2015 | Devenish | A61F 13/00063 604/360 |

\* cited by examiner

WOUND DRESSING CONTAINING HONEY AND COLLAGEN

RELATED APPLICATIONS

The present application is a continuation of U.S. patent application Ser. No. 14/031,716, filed Sep. 19, 2013, now U.S. Pat. No. 10,342,891, issued Jul. 9, 2019, which is incorporated by reference in its entirety.

FIELD OF THE INVENTION

The present invention relates to the formation of a complex wound dressing consisting of a saccharide, such as Manuka honey, in combination with collagen in order to suppress the efficacy of harmful enzymes called matrix metalloproteinases ("MMPs") that are present in chronic wounds.

BACKGROUND

The use of saccharides or sugars in liquid form, such as honey, is known to be effective as a dressing for wounds, burns and skin ulcers. Benefits include that inflammation, swelling and pain are quickly reduced, that sloughing of necrotic tissue occurs without the need for additional debridement, and that growth of tissues to repair the wound is stimulated. As a consequence, healing occurs rapidly with minimal scarring, and often without any necessity for skin grafting.

In addition to the use of saccharides in wound treatment, it is known that MMPs, which are part of the larger family of metalloproteinase enzymes, play an important part in wound healing. Although MMPs have the important role of breaking down proteins so that new tissue forms, when MMPs are present in a wound bed at too high a level, for too long a time, and in the wrong places, they begin to degrade proteins that are not their normal substrates. This can result in the unwanted destruction of beneficial proteins, such as growth factors, receptors and ECM proteins, that are essential for healing, and so ultimately impair healing. Substantial evidence has amassed that MMPs in general are highly elevated in wounds with delayed healing compared to acute healing wounds as discussed, for example, in Wounds International, "MMPs Made Easy" (Vol. 1, Issue 1, November 2009), which is incorporated herein by reference. The potentially damaging effects of these high levels is compounded by the fact that tissue inhibitors of metalloproteinases ("TIMPs") levels in chronic wounds are generally slightly lower than in acute wounds.

Collagen dressings are used to suppress MMP levels, but scientific literature and opinion shows that such advanced dressings cannot be used until wounds are cleansed of necrotic tissue. The most preferred methods of cleansing of necrotic tissue are often surgery, curettage or sharp debridement. However, it may not always be possible to use one of these methods on patients who are not suitable candidates for such fast and immediate debridement. Collagenase enzyme, a MMP, is itself sometimes used to promote debridement, which, of course, cannot be mixed with a collagen dressing because the collagen dressing will engage the MMP, collagenase, which is being inserted into the wound for debridement.

Given that collagen promotes wound healing, it would be advantageous to the patient to be able to make use of and benefit from a collagen dressing during the weeks that are usually required for non-sharp debridement. Accordingly, it would be beneficial if some means were to be found provide non-sharp debridement while at the same time applying collagen to the wound.

U.S. Pat. No. RE42,755 to Molan describes a wound dressing incorporating a honey composition that is at least 50% honey and mixed with a gelling agent to render it formable, pliable, flexible and moldable. Molan does not mention the MMP suppression effect of honey, nor does it suggest that the MMP suppression activity of honey may be synergistically augmented via the introduction of variable quantities of collagen.

U.S. Pat. No. 4,844,898 to Komori, U.S. Pat. No. 3,767,784 to Gluck, and U.S. Pat. No. 4,401,651 to Knutson also discuss saccharide compositions for use with wound dressings. Each of these references fails to recognize that the efficacy of saccharides is driven by the exertion of osmotic pressure. This osmotic pressure effect causes wound exudates to flood in from deep within tissue into the wound site, dissolving necrotic tissue and cleansing the wound. In addition, these patents were written prior to the introduction of the concept that MMPs are responsible for wound chronicity, and they do not mention collagen as a compositional additive to honey or any other saccharide.

Accordingly, a need exists for a composition that provides non-sharp debridement while also controlling the level of MMPs present in the wound.

SUMMARY OF THE INVENTION

In order to address the shortcomings of the prior art and in accordance with the present invention, a technology is described that provides non-sharp debridement of a wound while also controlling the level of MMPs present in the wound. Such debridement can be accomplished by the use of honey as a part of a wound healing package. Honey debrides via osmotic pressure, and its acidity that is well known tends to denature, at least temporarily, MMPs that lead to wound chronicity. At the same time, the inventors have found honey to be compatible with collagen dressings, in fact, it is synergistic with honey in the sense that collagen massively suppresses MMP activity.

Embodiments of the invention include a dressing for application to a wound that includes a wound contacting layer for contacting the wound surface. The wound contacting layer may comprise a mixture of a saccharide and an MMP suppressing material. In embodiments of the invention, the saccharide is honey, and the MMP suppressing material may be collagen. The collagen may be powdered collagen, a collagen gel or other form of collagen.

The saccharide mixture may include additional materials. For example, it is well known that the ability of the sugar to debride and loosen necrotic tissue in the wound is driven by the effect of the exertion of osmotic pressure. This osmotic pressure is directly related to the concentration of sugars at the wound surface. Thus it would be beneficial increase the concentration of sugar that comes into contact with the wound. Accordingly, it may be advantageous to combine cane sugar or other sugars with the honey and collagen mixture. This has the additional advantage of addressing usability issues of both honey and cane sugar. Pure honey may flow too fast and, if applied to a wound, is more likely to spill out of it, than stay in it, and this effect is only minimally improved upon via the use of a secondary dressing such as gauze. Likewise, pure crystalline or powder sugar has usability issue. For example, powdered sugar is messy in terms of application in a wound and a secondary bandage is most certainly needed. Accordingly, it would be beneficial if some means were to be found to attach or adhere cane sugar to a secondary dressing but without the use of sugar diluting adhesives or any non-sugar matter.

To address the usability issues of honey, it may also be advantageous to include other thickening or gelling components. In addition, in may be advantageous to include other materials have tissue health promoting properties. These additional materials may include materials having antibiotic effects, such as silver or silver compounds.

BRIEF DESCRIPTION OF THE DRAWINGS

The foregoing and other advantages of the invention will become apparent upon reading the following detailed description and upon reference to the drawings.

Figure 1:
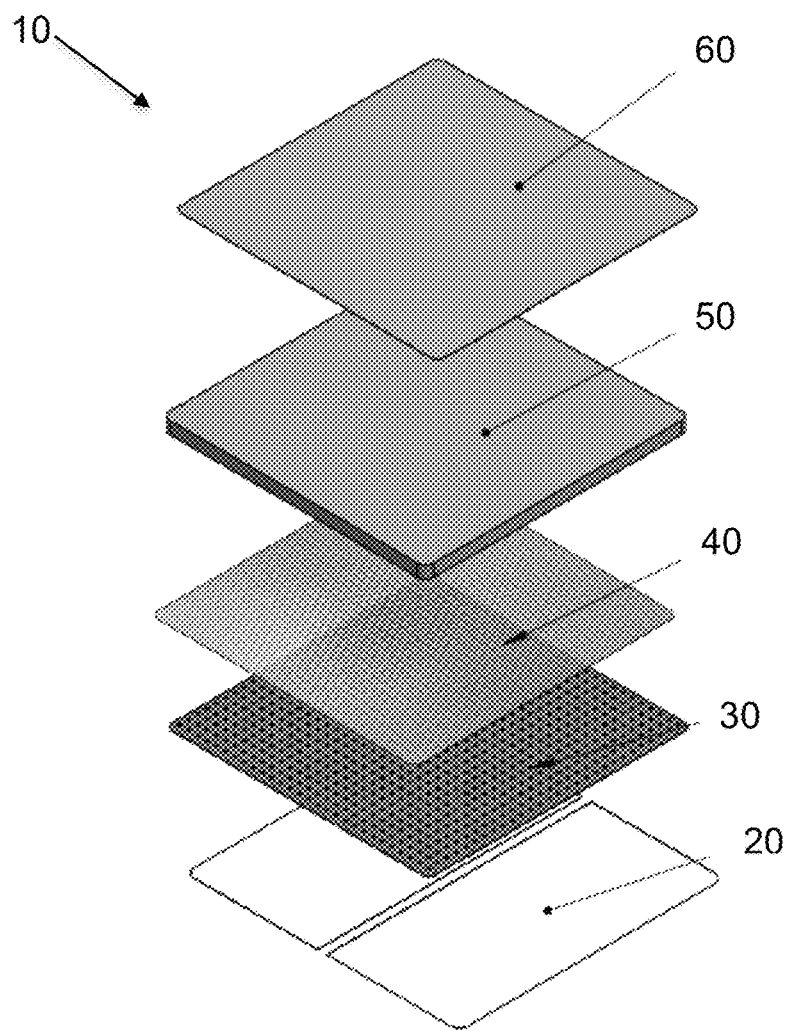
FIG. 1 is an exploded view of a wound dressing having various layers according to one embodiment of the invention.
Figure 2:
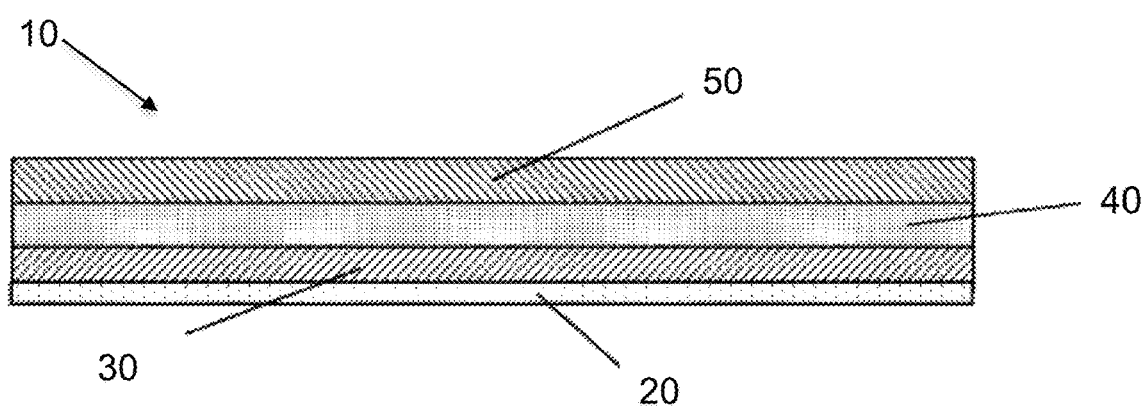
FIG. 2 is cut-away, side view of a wound dressing having various layers according to one embodiment of the invention.

The view of FIGS. 1 and 2 are intended to illustrate the composition of a wound dressing in accordance with embodiments of the present invention. The views are not to scale and are not intended to limit the dimensions or structure of the invention. While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions In embodiments of the invention, honey is mixed with collagen in order to form a wound contacting composition. This composition can be laminated to substrates of various types, for example, polyurethane foams, or super absorbent polymer films or papers. The use of such substrates may allow additional convenience in delivering the active agents.

In embodiments of the invention, the wound contacting composition may also include additional materials. These additional materials may include materials having known tissue health promoting properties. For example, the additional materials may include materials having antibiotic effects, such as silver or silver compounds. Other materials that may be added to the wound contacting composition include plant extracts, vitamins. enzymes, hormones, amino acids and minerals.

In addition, it may be advantageous to add materials that affect the viscosity and/or tackiness of the wound contacting composition. As discussed above, embodiments of the invention contemplate the addition of cane sugar to a composition containing honey and collagen. For purposes of the invention, cane sugar includes equivalent sugar obtained from other sources, for example, sugar derived from sugar beets. The sugar may be of various forms including crystalline sugar, powdered sugar, or syrup. Other materials affecting the viscosity or tackiness of the composition may also be used. Examples include, but are not limited to glycerine, petrolatum (white soft paraffin), gelatin, natural or artificial gum (such as gum arabic or tragacanth), ovalbumin (egg albumin), soya protein, casein, carbohydrate polymers (such as dextrin), natural waxes (such as beeswax, carnauba wax and candela wax), paraffin waxes, hydrocarbon polymers (such as polymers of ethylene and polyisobutylene), fatty acids and alcohols (such as stearic acid, stearyl alcohol and lanolin alcohols), and modified waxes (such as siliconyl beeswax), in addition to hydrophilic thickening and gelling agents (such as carrageenan derivatives and cellulose polymers).

Embodiments of a wound dressing in accordance with the present invention may be prepared in a variety of known manners. For example, a highly viscous mixture of honey, collagen and other components can be created by mixing the components in a sigma mixer. The mixture can then be extruded by a screw type extruder, or any other appropriate means, onto a substrate. The substrate is chosen so that it does not allow easy immediate ingress of the entire sugar mixture into the substrate.

FIGS. 1 and 2 illustrate an embodiment of the present invention. As shown, a dressing 10 in accordance with the present invention may include a backing layer 20. The backing layer provides protection for the dressing during manufacture and transportation and is removed prior to applying the dressing to a wound. The backing layer may be a laminated paper or another protective layer as would be apparent to one of ordinary skill in the art.

The dressing 10 may also include a wound contacting layer 30. Embodiments of the wound contacting layer 30 include various compositions a fluid saccharide material combined with collagen as described above. The fluid saccharide material may be honey, and more specifically Manuka honey. The wound contacting layer may also comprise other materials as described above.

The ratio of the honey, collagen and other materials may vary depending upon the desired viscosity of the layer. It is contemplated that the ratio of honey to other materials may be varied such that the resulting wound contacting layer comprises a solid, a liquid, a gel or a free-flowing particulate material.

In embodiments of the invention, the wound contacting layer 30 comprises greater than 95% by weight of honey and less than 5% by weigh of collagen. In further embodiments, the wound contacting layer comprises less than 50% by weight of honey, and more particularly may include between 10% and 45% by weight of honey. The remaining 55% to 90% of the composition is made up of collagen or a combination of collagen and other materials.

Various illustrative compositions of the wound contacting layer 30 are set forth below. Percentages are by weight.

Example 1: honey >99%, collagen <1%.
Example 2: honey 95%, collagen 5%;
Example 3: honey 70%, collagen 30%;
Example 4: honey 50%, collagen 50%;
Example 5: honey 30%, collagen 70%;
Example 6: honey 10%, collagen 90%;
Example 7: honey 10%, cane sugar 40%, collagen 50%;
Example 8: honey 10%, cane sugar 80%, collagen 10%;

Example 9: honey 45%, cane sugar 45%, collagen 10%;
Example 10: honey 45%, cane sugar 10%, collagen 45%;
Example 11: honey 30%, cane sugar 35%, collagen 35%;
Example 12: honey 98%, collagen 1%, other materials having tissue health enhancing properties 1%;
Example 13: honey 45%, collagen 5%, materials affecting the viscosity or tackiness of the composition 50%;
Example 14: honey 45%, collagen 5%, other materials having tissue health enhancing properties 5%, materials affecting the viscosity or tackiness of the composition 45%.

These examples are illustrative, and it will be understood by one of ordinary skill in the art that the invention includes compositions having different ratios of the listed materials or including additional materials not listed.

Alternatively, the wound contacting layer 30 may comprise two or more layers of having different compositions. For example, the wound contacting layer may have a first layer adjacent to the wound surface that contains only honey and cane sugar in order to stimulate debridement of the wound. The wound contacting layer may then include a second layer that contains honey, cane sugar and collagen, such that the layer including collagen, which provides for additional suppression of MMPs is exposed to the wound only after the first layer has dissolved.

As shown in FIGS. 1 and 2, the dressing 10 may also include a film layer 40. The film layer may comprise a polymer film, paper, a woven or non-woven fabric, or the like. The film layer may also include through apertures that allow fluid from the wound to pass through the film layer. The wound contacting 30 may be extruded onto, adhered to, laminated to, or encapsulate the film layer 40.

The dressing may also include an absorbent layer 50. The absorbent layer may be composed of polyurethane foam, cellulose fiber or another appropriate absorbent material. The absorbent layer 50 may be adhered or laminated to the film layer 40. Alternatively, the film layer 40 may be dispensed with, and the wound contacting layer 30 may be applied directly to the absorbent layer. Whether the wound contacting layer 30 is applied to a film layer 40 or directly an absorbent layer 50, the substrate is chosen so that it does not allow easy immediate ingress of the entire wound contacting composition into the substrate.

As shown in FIG. 1, the dressing may also include a cover layer 60. The cover layer may polymer film such as a polyurethane film. Alternatively the cover layer may be a woven or non-woven fabric or another appropriate covering material. The cover material may be fluid impervious in order to contain fluid absorbed by the dressing from the wound. The cover material may also be a breathable material.

FIGS. 1 and 2 illustrate the various layers as being coterminous. However, the layers may extend past one another. For example, the cover layer 60 shown in FIG. 1 may extend beyond the periphery of the wound contacting layer 30. A skin facing surface of the cover layer may be adhesive such that the cover layer serves to adhere to dressing to the patient's skin surrounding the wound.

What is claimed is:

1. A dressing for application to a wound comprising:
a wound contacting layer comprising:
a first layer consisting of honey having a first viscosity and a supplemental material; and
a second layer comprising the honey, the supplemental material, and a powdered collagen;
wherein the honey, the supplemental material, and the powdered collagen form a mixture in the wound contacting second layer having a viscosity that is greater than the viscosity of the honey.

2. The dressing of claim 1, wherein the supplemental material is cane sugar.

3. The dressing of claim 2, wherein the cane sugar comprises crystalline sugar.

4. The dressing of claim 2, wherein the cane sugar comprises powdered sugar.

5. The dressing of claim 2, wherein the cane sugar comprises a sugar syrup.

6. The dressing of claim 1, wherein the supplemental material has antimicrobial properties.

7. The dressing of claim 6, wherein the supplemental material comprises silver.

8. The dressing of claim 1, wherein the wound contact second layer comprises between 10% and 45% by weight of honey.

9. The dressing of claim 1, wherein the wound contacting second layer comprises greater than 90% by weight of honey.

10. The dressing of claim 9, wherein the wound contacting second layer comprises less than 10% by weight of collagen.

11. The dressing of claim 1, wherein the wound contacting second layer comprises between 40% and 80% by weight of the supplemental material.

12. The dressing of claim 1, wherein the wound contacting second layer comprises between 10% and 50% by weight of collagen.

13. A dressing for application to a wound comprising:
a wound contacting layer comprising honey having a first viscosity and powdered collagen;
a film layer;
an absorbent layer; and
a cover layer;
wherein the wound contacting layer is applied to the film layer, and
wherein the honey and powdered collagen form a mixture in the wound contacting layer having a viscosity that is greater than the viscosity of the honey.

14. The dressing of claim 13, wherein the wound contacting layer comprises:
a first layer adjacent to the wound surface, the first layer comprising honey and cane sugar; and
a second layer comprising honey, cane sugar and powdered collagen.

15. The dressing of claim 14, wherein the first layer of the wound contacting layer consists essentially of honey and cane sugar.

16. The dressing of claim 13, wherein the wound contacting layer comprises:
a first layer adjacent to the wound surface, the first layer comprising honey and a supplemental material; and
a second layer comprising honey, the supplemental material and powdered collagen.

17. The dressing of claim 13, wherein the wound contacting layer comprises:
a first layer adjacent to the wound surface, the first layer comprising honey and powdered collagen; and
a second layer comprising honey, a supplemental material and powdered collagen.

* * * * *